(12) United States Patent
Fan et al.

(10) Patent No.: US 6,543,657 B2
(45) Date of Patent: Apr. 8, 2003

(54) THERMAL MANIKIN

(75) Inventors: Jintu Fan, Kowloon (HK); Yi-song Chen, Kowloon (HK)

(73) Assignee: Hong Kong Polytechnic University, Kowloon (HK)

( * ) Notice: Subject to any disclaimer, the term of this patent is extended or adjusted under 35 U.S.C. 154(b) by 17 days.

(21) Appl. No.: 09/811,833

(22) Filed: Mar. 20, 2001

(65) Prior Publication Data

US 2002/0191669 A1 Dec. 19, 2002

(51) Int. Cl.⁷ .............................................. D06C 15/00
(52) U.S. Cl. ........................... 223/66; 223/70; 434/396; 434/395; 434/268
(58) Field of Search ..................... 223/66, 70; 434/396, 434/395, 268, 126

(56) References Cited

U.S. PATENT DOCUMENTS 5,409,382 A * 4/1995 Donnelly et al. ........... 434/262

* cited by examiner

*Primary Examiner*—John J. Calvert
*Assistant Examiner*—James G Smith
(74) *Attorney, Agent, or Firm*—Leydig, Voit & Mayer, Ltd.

(57) ABSTRACT

A thermal manikin has a closed perforated rigid frame covered by a breathable fabric extending over the frame and forming arms and legs. Water passages and a pump inside the manikin direct water around the manikin to simulate natural blood flow. The manikin is provided with a controller and sensor for measuring conditions inside and outside the manikin that enables simultaneous determination of Clo (thermal resistance of clothing placed on the manikin) and Im (the permeability index of the clothing).

12 Claims, 3 Drawing Sheets

THERMAL MANIKIN

BACKGROUND OF THE INVENTION

1. Field of the Invention

The invention relates to thermal manikins.

2. Description of Prior Art

Thermal comfort of clothing systems can be evaluated subjectively by wearer trials but such trials can expose the wearer to danger in extreme conditions testing. Objective testing can also be carried out using flat plates and cylindrical methods to evaluate thermal properties of simple clothing, but practically applying results of such test in evaluating thermal comfort of clothing is not normally very useful. Thermal manikins have therefore been developed for providing more useful results.

Thermal comfort of clothing is mainly determined by the heat and moisture transferring through the clothing system. In order to optimize the clothing system so as to achieve maximum thermal comfort, considerable research has been carried out on the heat and moisture transfer through clothing systems over many years. The best simulation of a human body wearing clothing is achieved by testing clothing systems on thermal manikins. Presently thermal manikins can comprise these types. The first type are standing and non-perspiring. The second type are movable but non-perspiring.

The first or second types have been made perspiring by wetting such that the perspiration is supplied, in effect, from outside to the 'skin' using sprinklers or pipes.

Such methods of simulating perspiring tend to be poor in reproducibly Although manikins are useful tools for evaluating thermal comfort of overall clothing systems.

The third type of manikins are standing and perspiring. They are not widely used because of their relatively high cost.

SUMMARY OF THE INVENTION

It is an object of the invention to overcome or at least to reduce this problem.

According to one aspect of the invention there is provided a thermal manikin having a rigid perforated main frame, a closed breathable fabric skin extending over the frame and forming arms and legs of the manikin, a heater mounted inside the frame, water passages inside the manikin to direct water towards extremities of the arm and legs, and a pump to circulate water around the manikin to simulate a natural blood flow of a human body.

The heater is preferably mounted in a chest of the manikin.

The arms and legs may be arranged so that they can be swung backwards and forwards to simulate walking.

An externally mounted topping-up gauge may be provided to enable measurable quantities of water to be added to the inside of the manikin to provide accurate determinations of how much water has used during a testing period.

According to another aspect of the invention there is provided a method of measuring thermal comfort of clothes which comprises clothing a thermal manikin, in which the manikin has a rigid perforated main frame, a closed breathable fabric skin extending over the frame and forming arms and legs of the manikin, a heater mounted inside the frame, water passages inside the manikin to direct water towards extremities of the arms and legs, and a pump to circulate water around the manikin to simulate a natural blood flow of a human body, and simultaneously determining Clo (thermal resistance of the clothing) and Im (the permeability index of the clothing).

BRIEF DESCRIPTION OF THE DRAWINGS

A thermal manikin according to the invention will now be described by way of example with reference to the accompanying drawings in which.

DESCRIPTION OF THE PREFERRED EMBODIMENT

Figure 1:
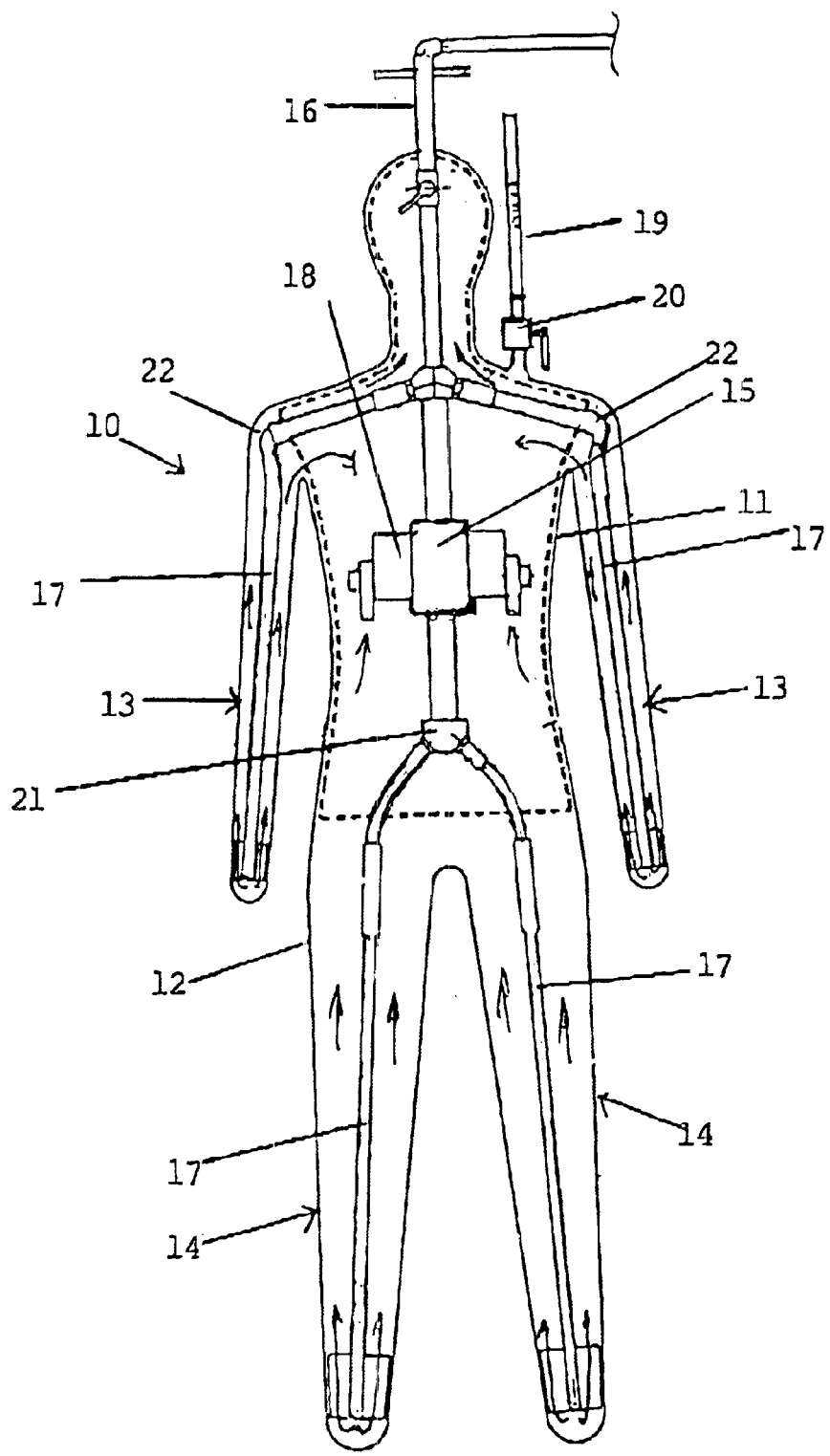
FIG. 1 is a front schematic view of the manikin.
Figure 2:
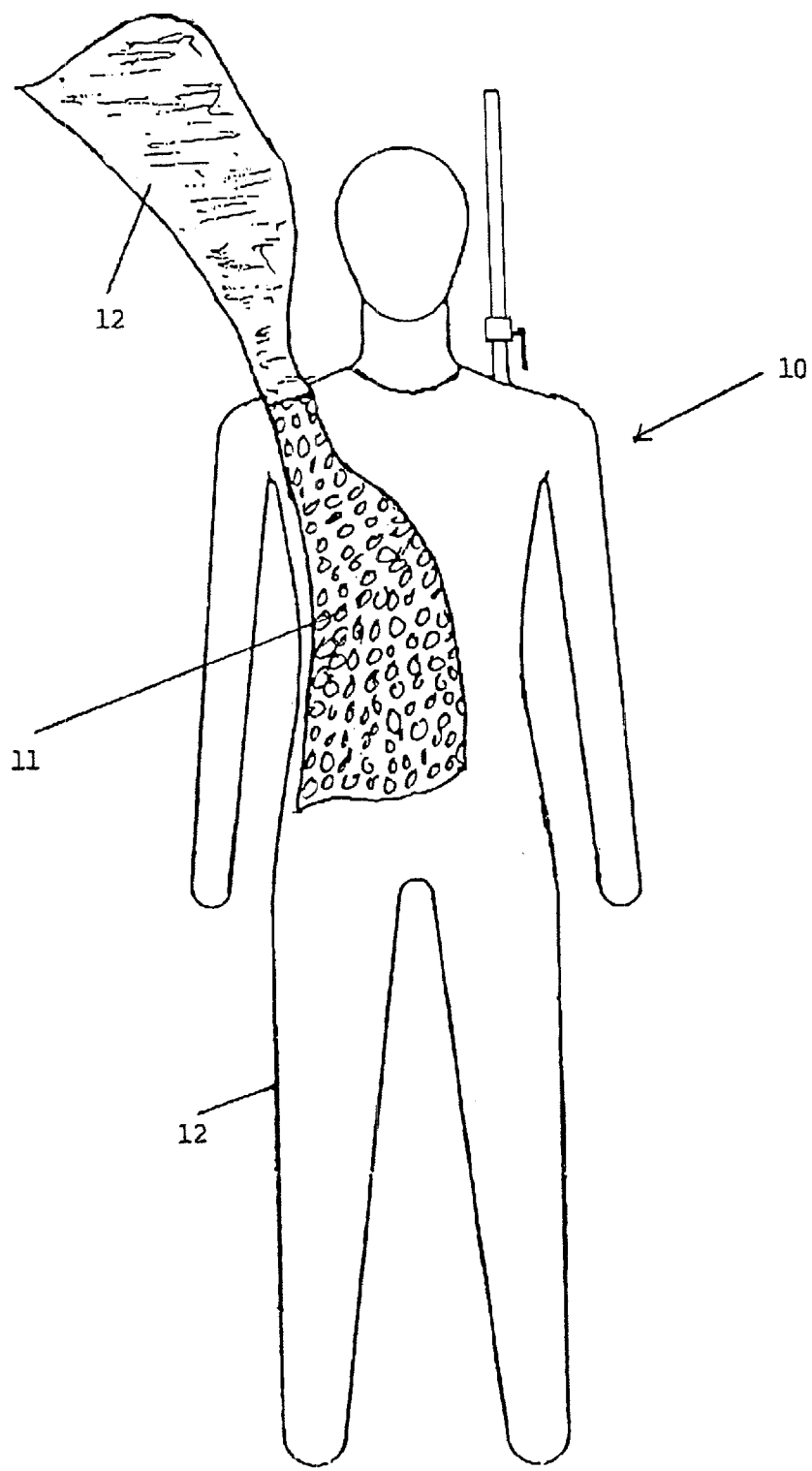
FIG. 2 is front external view of the manikin.

Referring to the drawings, in FIG. 1 the manikin 10 is made in size and configuration to replicate a typical man. The manikin is 1.7 meters in height and has an outer surface area of approximately 1.5 meters. The outer surface, or skin, has a soft feel and the body is flexible. The manikin has a perforated rigid plastic main frame 11 forming a trunk and head. The main frame 11 is covered by a breathable sealed skin 12, that also forms arms 13 and legs 14, which in use is filled with water. The manikin is shown in FIG. 2 with a piece of skin 'torn away' to show part of the main frame 11. The skin 12 is made of three layers, an outer layer of nylon, an inner layer of knitted fabric and a central layer of microporous polytetrafluoroethylene. Suitable materials are already known and used for specialist sports clothing, such materials are available and sold as GORETEX (trade mark) material.

A water heater 15 is inside the frame 11, approximately where a human heart would be situated, and is connected to a supply pipe 16. The pipe 16 provides a hanging support for the manikin. Water passages inside the manikin are provided by a network of pipes 17 that lead from the heater 15 to extremities of the arms and legs. A pump 18 is used to pump water along the pipes 17 to provide a flow of water (see arrows in FIG. 1) around the inside of the manikin to simulate a natural blood flow of a human body. A topping-up gauge 19 is connected by a manually operable valve 20 to allow the manikin to be re-filled to a top up line with measured quantities of water, as required from time to time. This enables the amount of water used to readily determined after each testing period.

When the manikin is supported by the pipe 16, as described above, the arms and legs are generally free to swing backwards and forwards. Swivellable joints 21 and 22 allow suitable relative movement between the pipes 17. Thus for simulating walking suitable mechanical 'pushers' (not shown) are positioned to pull and push the arms and legs, as required.

In use, the manikin's core temperature is controlled to be 37° C. Normally the manikin is suspended inside a box frame, that may have outer walls to form a cabinet surrounding the manikin. The manikin can produce gaseons 'perspiration' to simulate human sweating which will vary according to the amount and type of clothing that is worn.

Figure 3:
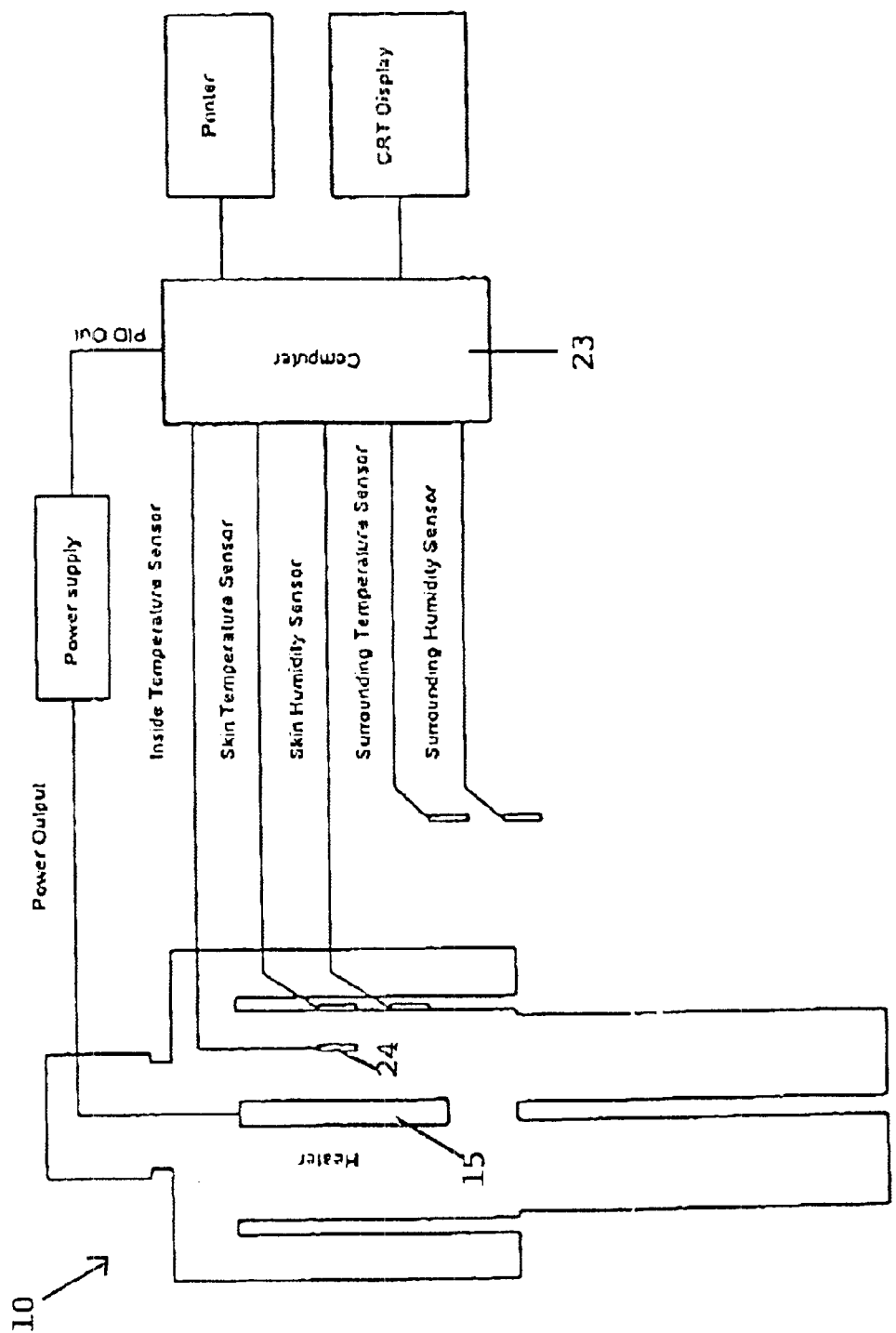
FIG. 3 is a schematic diagram of a control and measurement system for the manikin.

In FIG. 3, the manikin 10 is provided with a number of sensors (known per se) for supplying a computer 23 with information for determining operating conditions during testing. The computer is programmed to control a power supply to the heater 15, while responding to a temperature sensor 24 inside the manikin, to maintain water temperature inside the manikin at 37° C.; typically the normal body temperature of a human body. In use, the manikin produces heavy gaseous 'perspiration'. The insensible perspiration of a human body is around 30 g/h, and when sweating can reach 1000 g/h. The perspiration of the manikin varies with the amount and type of clothing worn and can operate over a range of normal human perspiration. It is possible, by providing additional separately controllable pumps or adjustable-valves (not shown) for the pipes 17, to vary the skin temperature distribution at the surface of the skin 12 where required. As the manikin is supported by the pipe 16 and hangs below the pipe, clothing can be easily put on and taken off the manikin. As already mentioned, the limbs of the manikin can by arranged to be mechanically moved to simulate walking.

The computer is programmed to simultaneously determine Clo (thermal resistance) and Im (permeability index):

$$Clo = \frac{K \cdot \Delta T}{Wt}$$

Where k is a constant of proportionality, $\Delta T$ is the temperature difference between the skin and surrounding environment, and $W_t$ is the dry heat loss. $W_T$ is the dry heat loss calculated from the total heat loss minus the heat loss due to perspiration.

The Im value is determined by the following equation:

$$W = \frac{K}{Clo}(\Delta T + I_m \cdot S \cdot \Delta P)$$

Where C is a constant and equals 22° C./mmHg, $\Delta P$ is the vapour pressure difference between the skin at its temperature and the environment, and W is the total heat loss.

The quantity of water that evaporates during each testing cycles, as explained above, is determined by 'topping up' the water inside the manikin using the topping up gauge 19 after each testing cycle.

The Table below shows typical test results for the described manikin:

| Clothing | Ts | Te | Hs | He | W | Q | Clo | Clo DV | Im | Im DV |
|---|---|---|---|---|---|---|---|---|---|---|
| Nude | 35.3 | 28.6 | 86.0 | 67.3 | 360.5 | 410 | 0.64 | 0.03 | 0.43 | 0.02 |
| | 35.3 | 28.6 | 85.8 | 66.4 | 351.0 | 400 | 0.66 | | 0.43 | |
| | 35.3 | 28.7 | 85.5 | 66.5 | 345.0 | 395 | 0.66 | | 0.44 | |
| | 35.2 | 28.8 | 86.4 | 66.8 | 344.8 | 405 | 0.71 | | 0.47 | |
| | 35.1 | 28.5 | 86.7 | 67.0 | 344.4 | 400 | 0.70 | | 0.46 | |
| Underwear | 35.8 | 28.1 | 82.7 | 63.1 | 298.2 | 340 | 0.88 | 0.05 | 0.47 | 0.04 |
| | 35.9 | 28.1 | 83.1 | 63.2 | 296.0 | 320 | 0.78 | | 0.39 | |
| | 36.0 | 28.1 | 83.0 | 64.2 | 293.1 | 310 | 0.76 | | 0.37 | |
| | 36.0 | 27.8 | 82.6 | 59.6 | 294.0 | 320 | 0.84 | | 0.39 | |
| | 35.8 | 27.5 | 82.6 | 60.3 | 296.3 | 315 | 0.81 | | 0.37 | |
| Underwear + shirt | 36.4 | 28.3 | 87.3 | 57.8 | 279.2 | 310 | 0.91 | 0.03 | 0.36 | 0.02 |
| | 36.3 | 27.8 | 87.1 | 57.1 | 278.2 | 300 | 0.89 | | 0.34 | |
| | 36.3 | 27.8 | 87.0 | 57.5 | 278.9 | 300 | 0.89 | | 0.34 | |
| | 36.2 | 27.8 | 87.3 | 57.2 | 281.4 | 295 | 0.83 | | 0.31 | |
| | 36.2 | 27.5 | 87.5 | 57.4 | 281.5 | 295 | 0.86 | | 0.32 | |
| Underwear + shirt + suit | 36.7 | 27.0 | 92.9 | 59.4 | 196.4 | 195 | 1.16 | 0.11 | 0.25 | 0.03 |
| | 36.6 | 27.0 | 92.7 | 61.4 | 195.3 | 205 | 1.27 | | 0.30 | |
| | 36.5 | 26.8 | 92.7 | 61.5 | 197.8 | 200 | 1.20 | | 0.27 | |
| | 36.4 | 26.7 | 92.4 | 61.1 | 204.4 | 200 | 1.11 | | 0.25 | |
| | 36.5 | 26.7 | 92.7 | 60.5 | 212.2 | 195 | 0.98 | | 0.22 | |

Where $T_e$ is the mean "skin" temperature, $T_e$ the mean ambient temperature, Hs the mean "skin" humidity, He the mean ambient humidity, W the total heat loss, Q the total water loss due to perspiration, Clo DV the standard deviation of Clo value, Im DV the standard deviation of Im value.

We claim:

1. A thermal manikin having a human body shape, comprising:
    a rigid perforated main frame,
    a closed breathable fabric skin covering the frame and defining an internal volume of the manikin, including arms and legs of the manikin,
    a heater mounted inside the frame,
    water passages inside the manikin to direct water towards extremities of the arms and legs, and
    a pump to circulate water through the water passages and around the manikin to simulate natural blood flow of a human body.

2. The thermal manikin according to claim 1, in which the heater is mounted in a chest of the manikin.

3. The thermal manikin according to claim 1, in which the arms and legs can be swung backwards and forwards to simulate walking.

4. The thermal manikin according to claim 1, including an externally mounted topping-up gauge for adding quantities of water inside of the internal volume of the manikin and for determining how much water has been used during a testing period.

5. The thermal manikin according to claim 1, wherein the water passages comprise conduits extending into the arms and legs and open at ends at the extremities of the arms and legs for discharging water.

6. The thermal manikin according to claim 5, wherein the conduits include swivel joints for movement of the arms and legs to simulate movement of a person replicated by the manikin.

7. The thermal manikin according to claim 5, wherein the conduits join into a single conduit that passes through a head of the manikin as a hanging support for suspending the manikin during use.

8. The thermal manikin according to claim 1, wherein the rigid perforated main frame defines a torso of the manikin.

9. The thermal manikin according to claim 1, wherein the closed breathable fabric skin has multiple laminated layers.

10. The thermal manikin according to claim 9, wherein the closed breathable fabric skin includes a layer of polytetrafluoroethylene sandwiched between inner and outer layers.

11. The thermal manikin according to claim 1, including a plurality of sensors attached to the breathable fabric skin outside the internal volume of the manikin for measuring moisture flow through the breathable fabric skin.

12. The thermal manikin according to claim 11, including a temperature sensor inside the internal volume of the manikin.

* * * * *